United States Patent [19]

Van Horn et al.

[11] 4,140,698
[45] Feb. 20, 1979

[54] 1,2-DIHYDRO-3H-PYRROLO[1,2-a]PYRROLE-1-NITRILES

[75] Inventors: Albert R. Van Horn, Los Altos; Pasquale G. Gallegra, San Jose, both of Calif.

[73] Assignee: Syntex (USA) Inc., Palo Alto, Calif.

[21] Appl. No.: 910,979

[22] Filed: May 30, 1978

Related U.S. Application Data

[62] Division of Ser. No. 818,377, Jul. 25, 1977.

[51] Int. Cl.$^2$ .......................................... C07D 487/04
[52] U.S. Cl. ..................... 260/326.55 M; 260/326.25; 260/326.5 B; 424/274
[58] Field of Search ................ 260/326.5 B, 326.55 M

[56] References Cited

U.S. PATENT DOCUMENTS

| | | | |
|---|---|---|---|
| 4,087,539 | 5/1978 | Muchowski et al. | 260/326.25 |
| 4,089,969 | 5/1978 | Muchowski et al. | 260/326.25 |
| 4,097,579 | 6/1978 | Muchowski et al. | 260/326.25 |

OTHER PUBLICATIONS

Brandange et al; Chem. Abs. vol. 76:25024t (1972).

*Primary Examiner*—Nicholas S. Rizzo
*Assistant Examiner*—Mary Lee
*Attorney, Agent, or Firm*—Gerard A. Blaufarb; William B. Walker

[57] ABSTRACT

5-Substituted-1,2-dihydro-3H-pyrrolo[1,2-a]pyrrole-1-carboxylic acids of the formula

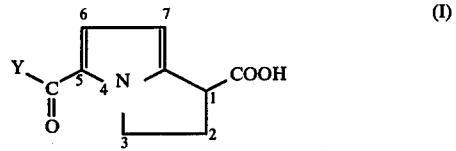

(I)

wherein Y is a moiety selected from the group consisting of

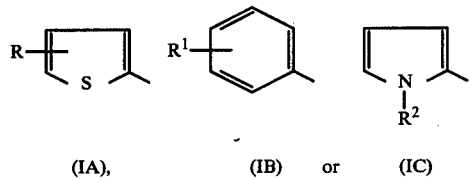

(IA), (IB) or (IC)

in which
R is hydrogen, methyl, chloro or bromo, the R substitution being at the 3, 4 or 5 positions of the thiophene ring,
$R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the aroyl group, and
$R^2$ is hydrogen or a lower alkyl group having from 1 to 4 carbon atoms, are prepared, by hydrolysis, from their corresponding nitriles.

4 Claims, No Drawings

1,2-DIHYDRO-3H-PYRROLO[1,2-A]PYRROLE-1-NITRILES

This is a division of application Ser. No. 818,377, filed July 25, 1977.

The present invention relates to a method for the preparation of 5-substituted-1,2-dihydro-3H-pyrrolo[1,2-a]pyrrole-1-carboxylic acids of the formula:

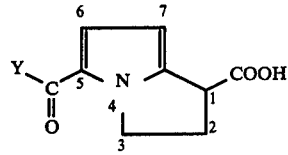

wherein Y is a moiety selected from the group consisting of

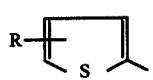  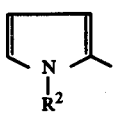

(IA), (IB) or (IC)

in which
R is hydrogen, methyl, chloro or bromo, the R substitution being at the 3, 4 or 5 positions of the thiophene ring,
$R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the aroyl group, and
$R^2$ is hydrogen or a lower alkyl group having from 1 to 4 carbon atoms.

The compounds of Formula (I) are prepared by converting, hydrolytically, the corresponding 5-substituted-1,2-dihydro-3H-pyrrolo-[1,2-a]pyrrole-1-nitriles of the formula

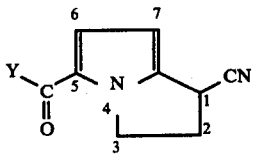

wherein Y is defined as above.

The conversion of the compounds of Formula (II) to the compounds of Formula (I) may be depicted schematically as follows:

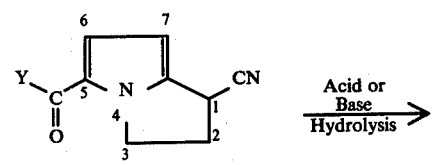

The "end-products" of Formula (I) have been previously described in co-pending U.S. Application Ser. Nos. 771,283 now U.S. Pat. No. 4,087,539,

[partial formula (IA), 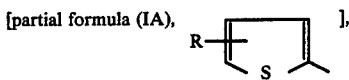], 771,286 now U.S. Pat. No. 4,089,969,

[partial formula (IB), 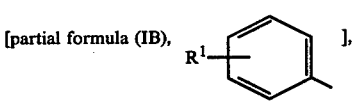], and 783,090, now U.S. Pat. No. 4,097,579,

[partial formula (IC), 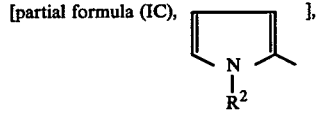], the preparation thereof being by methods other than those disclosed herein.

The compounds of Formula (I) are useful as antiinflammatory agents, analgetic agents, platelet aggregation inhibitors, fibrinolytic agents, and as smooth muscle relaxants. They can be used both prophylactically and therapeutically.

The "starting materials" of Formula (II) are prepared according to the preparations set forth below.

The hydrolysis conversion of the compounds of Formula (II) to the compounds of Formula (I) can be carried out under a variety of acidic or basic conditions, generally those conditions employed by those skilled in the art for the conversion of nitriles to carboxylic acids.

If the hydrolysis conversion is carried out under acidic conditions it is generally preferred that it be done with a strong mineral acid, e.g., phosphoric acid, sulfuric acid, hydrochloric acid, hydrobromic acid, and the like, in the presence of water, with or without the presence of an organic acid, e.g., acetic acid, formic acid, propionic acid, and the like. If desired other organic solvents miscible with the mineral acid (and the water and the organic acid, if the latter is used) can be used. Suitable organic solvents are methanol, ethanol, ethylene glycol, dimethylsulfoxide, dioxane, tetrahydrofuran, ethylene glycol dimethyl ether (glyme), diethylene glycol dimethyl ether (diglyme), and the like. The reaction is preferably carried out under an inert atmosphere, e.g., nitrogen, argon, and the like, with nitrogen being the most preferred. The reaction times and temperatures are not critical and depend, as will be apparent to those skilled in the art, on the reactants and other ingredients of the reaction mixture) employed. Thus, the reaction time can be from about one minute to about 10 hours with about five minutes to about three hours being preferred; and the reaction temperature from about 60° C. to about 200° C., with about 80° C. to about 120° C. being preferred.

If the hydrolysis conversion is carried out under basic conditions, it is generally preferred that it be done with a strong base, preferably a mineral base, e.g., potassium hydroxide, sodium hydroxide, lithium hydroxide, and the like, in the presence of water. Advantageously, water miscible organic solvents, e.g., 2-methoxyethanol, methanol, ethanol, ethylene glycol, dimethylsulfoxide, and the like are used to facilitate solution of the reactants. The reaction is preferably carried out under an inert atmosphere, e.g., nitrogen, argon, and the like, with nitrogen being the most preferred. The reaction times and temperatures are not critical and depend, as will be apparent to those skilled in the art, on the reactants (and other ingredients of the reaction mixture) employed. Thus the reaction time can be from about 5 minutes to about 2 hours, with about 30 minutes to about 1 hour being preferred; and the reaction temperature from about 60° C. to reflux temperature with about 70° C. to reflux temperature being preferred.

Isolation, separation, and purification of the desired compound of Formula (I) from the reaction mixture containing it can be effected by any suitable separation or purification procedure, such as, for example, extractions, filtration, evaporation, distillation, crystallization, thin-layer chromatography, or column chromatography, high pressure liquid chromatography, and the like, or a combination of these procedures. Illustrations of suitable isolation, separation and purification procedures can be had by reference to the Examples (and Preparations) herein below. However, other isolation, separation and isolation procedures, could of course, also be used.

Where necessary, preparations and examples are repeated to prepare additional material for subsequent preparations and examples.

The following Examples (and Preparations) illustrate the invention but are not intended to limit its scope. Unless otherwise stated, temperatures are room or ambient temperature (about 20° C. to about 30° C.).

PREPARATION 1

A. To a mixture of 8.21 g of formaldehyde solution (37% aqueous) and 8.84 g of dimethylamine hydrochloride there is added 11.5 g of N-hydroxyethylpyrrole (see Shun-Ichi Murahashi et al., J.C.S. Chem Comm., 1974, 931–932) over a period of about 8 minutes whilst agitating and keeping the temperature below 60° C., with cooling if necessary. The temperature is permitted to drop to room temperature and the reaction mixture is agitated at room temperature for 15 hours, followed by the addition of 16 ml of 25% aqueous sodium hydroxide solution, agitation for 5 minutes, and the addition of 19 ml of methylene chloride and 20 ml of water. The organic layer is separated and the aqueous layer is extracted with 19 ml of methylene chloride. The organic portions are combined and washed with a mixture of 11 ml of saturated aqueous sodium chloride solution and 8 ml of water. The washed organic layer is dried over anhydrous sodium sulfate and the solvent is removed under vacuum to yield 17.2 g of an orange-yellow oil which, upon purification on a silica gel chromatography column (using 10% methanol in methylene chloride as solvent) yielded 12.9 g of 1-hydroxyethyl-2-[(N,N-dimethylamino)methyl]-pyrrole, having the following analysis:

Calculated: C, 64.25%, H, 9.59%; N, 16.65%. Found: C, 63.39%; H, 10.14%; N, 16.46%.

B. To 100 ml of acetone there is added 21.5 g of 1-hydroxyethyl-2-[(N,N-dimethylamino)methyl]-pyrrole, and to this mixture at 0° C., there is added 16.4 g of dimethylsulfate, whilst keeping the temperature below 2° C. during the addition. The temperature is then permitted to rise to room temperature and the reaction mixture agitated at room temperature for one hour. The thus-obtained reaction mixture is then added to a hot (about 90° C.) solution of 12.6 g of sodium cyanide in 27 ml of water, the addition being at such a rate, while at the same time distilling the solvent off, that the internal reaction flask temperature is kept at about 90°–95° C. When the addition is complete, the mixture is brought to reflux and heated under reflux for 15 minutes. The mixture is cooled to 25° C., followed by the addition of 40 ml of water and 60 ml of methylene chloride. The organic layer is separated, washed with 30 ml of a mixture of 50:50 saturated aqueous sodium chloride:water, the water layer is extracted twice with 30 ml of methylene chloride, and the combined organic layers are dried over anhydrous sodium sulfate and the solvent removed under vacuum to yield 21 g of a brown oil which upon purification on a silica gel chromatography column (using 50:50-ethyl acetate:hexane as solvent) yielded 13 g of 1-hydroxyethylpyrrole-2-acetonitrile having the following analysis:

Calculated: C, 63.98%; H, 6.71%; N, 18.66%. Found: C, 63.91%; H, 6.76%; N, 18.91%.

C. 1.6 G of 1-hydroxyethylpyrrole-2-acetonitrile is charged to a mixture of 12 ml of methylene chloride and 1.3 g of triethylamine, the flask being purged with nitrogen and the contents thereof being cooled to −10° C. 1.34 G of methanesulfonyl chloride is then added, whilst maintaining the temperature below 0° C., and the reaction mixture is agitated at 0° C., for 15 minutes. To the reaction mixture is added 10 ml of a mixture of 50:50-saturated aqueous sodium chloride solution:water, followed by extracting four times with 15 ml portions of methylene chloride and washing with dilute aqueous sodium chloride solution, drying over anhydrous sodium sulfate and removing the solvent under vacuum to yield 2.52 g of crude 1-(2'-methanesulfonylethane)-pyrrole-2-acetonitrile which is added to a mixture of 35 ml of acetonitrile and 3.76 g sodium iodide. The thus-obtained mixture is heated to 77° C. for one hour, cooled to 25° C., and 15 ml. of methylene chloride is added thereto. The organic salts are filtered off and washed with methylene chloride. The solvent is removed from the filtrate under vacuum, leaving a residue which is taken up in a mixture of 30 ml of methylene chloride and 30 ml of dilute aqueous sodium chloride solution. The organic layer obtained is dried over anhydrous sodium sulfate and the solvent removed under vacuum to yield 2.85 g of crude 1-(2-iodoethane)-pyrrole-2-acetonitrile, 2.7 g of which, dissolved in 10 ml of dimethylformamide, is added slowly, keeping the temperature below 15° C., to a suspension of 0.24 g of sodium hydride (obtained from 0.48 g of a 50% oil dispersion) in 10 ml of dimethylformamide. The reaction slurry, under a nitrogen atmosphere, is agitated for one hour at 20° C., followed by the addition of 35 ml of water and extracted with five 20 ml portions of diethyl ether. The organic extracts are combined and dried over sodium sulfate, followed by removal of the solvent at atmospheric pressure to yield 1.4 g of a brown oil which upon purification on a silica gel chromatography column (using 3:1-hexane:ethyl acetate as solvent) yielded 1 g of 1,2-dihydro-3H-pyrrolo-[1,2-a]pyrrole-1-nitrile having a melting point of 44°–45° C. (crystallized from ethanol) and the following analysis:

Calculated: C, 72.70%; H, 6.10%; N, 21.20%. Found: C, 72.72%; H, 6.25%; N, 21.17%.

PREPARATION 2

250 G of 2-thenoyl chloride [prepared according to the method of L. D. Jones and C. D. Hurd, J. Am. Chem. Soc, 43, 2444 (1921)] is charged to 1500 ml of tetrahydrofuran. The mixture is cooled to 0° C., and 1217 ml of 40% aqueous dimethylamine solution is added whilst keeping the temperature below 20° C. The reaction mixture is stirred for 15 minutes followed by removal of the tetrahydrofuran under vacuum, extraction of the aqueous solution with two portions of 1500 ml methylene chloride, drying over anhydrous sodium sulfate and removal of the solvent under vacuum. The residue remaining is distilled at 146° C., at 9 mm Hg pressure to yield 227.3 g of N,N-dimethyl-2-thienylcarboxyamide having a melting point of 40°–41.5° C.

In like manner substituting a stoichiometric equivalent amount of benzoyl chloride,
o-toluoyl chloride,
m-toluoyl chloride,
p-toluoyl chloride,
p-methoxybenzoyl chloride,
o-chlorobenzoyl chloride,
m-chlorobenzoyl chloride,
p-chlorobenzoyl chloride,
o-fluorobenzoyl chloride,
m-fluorobenzoyl chloride,
p-fluorobenzoyl chloride,
3-chloro-2-thenoyl chloride,
4-chloro-2-thenoyl chloride,
5-chloro-2-thenoyl chloride,
3-bromo-2-thenoyl chloride,
4-bromo-2-thenoyl chloride,
5-bromo-2-thenoyl chloride,
3-methyl-2-thenoyl chloride,
4-methyl-2-thenoyl chloride,
5-methyl-2-thenoyl chloride,
2-pyrroyl chloride,
N-methyl-2-pyrroyl chloride, and
N-n-butyl-2-pyrroyl chloride, for 2-thenoyl chloride, there are obtained N,N-dimethyl-2-benzoylcarboxamide,
N,N-dimethyl-2-O-toluoylcarboxamide,
N,N-dimethyl-2-m-toluoylcarboxamide,
N,N-dimethyl-2-p-toluoylcarboxamide,
N,N-dimethyl-2-p-methoxybenzoylcarboxamide,
N,N-dimethyl-2-o-chlorobenzoylcarboxamide,
N,N-dimethyl-2-m-chlorobenzoylcarboxamide,
N,N-dimethyl-2-p-chlorobenzoylcarboxamide,
N,N-dimethyl-2-o-fluorobenzoylcarboxamide,
N,N-dimethyl-2-m-fluorobenzoylcarboxamide,
N,N-dimethyl-2-p-fluorobenzoylcarboxamide,
N,N-dimethyl-2-(3-chloro-2-thienyl)carboxamide,
N,N-dimethyl-2-(4-chloro-2-thienyl)carboxamide,
N,N-dimethyl-2-(5-chloro-2-thienyl)carboxamide,
N,N-dimethyl-2-(3-bromo-2-thienyl)carboxamide,
N,N-dimethyl-2-(4-bromo-2-thienyl)carboxamide,
N,N-dimethyl-2-(5-bromo-2-thienyl)carboxamide,
N,N-dimethyl-2-(3-methyl-2-thienyl)carboxamide,
N,N-dimethyl-2-(4-methyl-2-thienyl)carboxamide,
N,N-dimethyl-2-(5-methyl-2-thienyl)carboxamide,
N,N-dimethyl-2-(2-pyrroyl)carboxamide,
N,N-dimethyl-2-(N-methyl-2-pyrroyl)carboxamide, and
N,N-dimethyl-2-(N-n-butyl-2-pyrroyl)carboxamide, respectively,

PREPARATION 3

1.77 G of N,N-dimethyl-2-thienylcarboxamide is charged to a mixture of 12.2 ml of 1,2-dichloroethane and 1.74 g of phosphorus oxychloride. The mixture is purged with nitrogen and heated to reflux for 1½ hours. After cooling to 25° C. a solution of 0.95 g of 1,2-dihydro-3H-pyrrolo-[1,2-a]pyrrole-1-nitrile in 4.4 ml of 1,2-dichloroethane is added and the thus-obtained solution is heated at reflux for 10 hours, after which time it is cooled to 25° C. To the cooled solution there is added a solution of 5.12 g of sodium acetate in 48 ml of water followed by heating to reflux for one hour, under vigorous agitation, cooling to room temperature and separation of the organic layer. The water layer is extracted twice with 20 ml portions of methylene chloride and each organic layer is washed with 20 ml of dilute aqueous sodium carbonate solution and then with 20 ml of dilute aqueous sodium chloride solution. The combined organic solutions are dried over anhydrous sodium sulfate and the solvent is removed under vacuum to yield 2.4 g of a brown oil which upon purification on a silica gel chromatography column (using 2.5:1-hexane:ethyl acetate as solvent) yielded 1.45 g of 5-(2-thenoyl)-1,2-dihydro-3H-pyrrolo[1,2-a]pyrrole-1-nitrile having a melting point of 106°–107.5° C., (crystallized from ethanol) and the following analysis:

Calculated: C, 64.44%; H, 4.16%; N, 11.56%; S, 13.24%. Found: C, 64.54%; H, 4.10%; N, 11.48%; S, 13.46%.

In like manner substituting a stoichiometric equivalent amount of

N,N-dimethyl-2-benzoylcarboxamide,
N,N-dimethyl-2-O-toluoylcarboxamide,
N,N-dimethyl-2-m-toluoylcarboxamide,
N,N-dimethyl-2-p-toluoylcarboxamide,
N,N-dimethyl-2-p-methoxybenzoylcarboxamide,
N,N-dimethyl-2-o-chlorobenzoylcarboxamide,
N,N-dimethyl-2-m-chlorobenzoylcarboxamide,
N,N-dimethyl-2-p-chlorobenzoylcarboxamide,
N,N-dimethyl-2-o-fluorobenzoylcarboxamide,
N,N-dimethyl-2-m-fluorobenzoylcarboxamide,
N,N-dimethyl-2-p-fluorobenzoylcarboxamide,
N,N-dimethyl-2-(3-chloro-2-thienyl)carboxamide,
N,N-dimethyl-2-(4-chloro-2-thienyl)carboxamide,
N,N-dimethyl-2-(5-chloro-2-thienyl)carboxamide,
N,N-dimethyl-2-(3-bromo-2-thienyl)carboxamide,
N,N-dimethyl-2-(4-bromo-2-thienyl)carboxamide,
N,N-dimethyl-2-(5-bromo-2-thienyl)carboxamide,
N,N-dimethyl-2-(3-methyl-2-thienyl)carboxamide,
N,N-dimethyl-2-(4-methyl-2-thienyl)carboxamide,
N,N-dimethyl-2-(5-methyl-2-thienyl)carboxamide,
N,N-dimethyl-2-(2-pyrroyl)carboxamide,
N,N-dimethyl-2-(N-methyl-2-pyrroyl)carboxamide, and
N,N-dimethyl-2-(N-n-butyl-2-pyrroyl)carboxamide, for N,N-dimethyl-2-thienylcarboxamide, there is obtained 5-benzoyl-1,2-dihydro-3H-pyrrolo[1,2-a]pyrrole-1-nitrile,
5-o-toluoyl-1,2-dihydro-3H-pyrrolo[1,2-a]pyrrole-1-nitrile,
5-m-toluoyl-1,2-dihydro-3H-pyrrolo[1,2-a]pyrrole-1-nitrile,
5-p-toluoyl-1,2-dihydro-3H-pyrrolo[1,2-a]pyrrole-1-nitrile,
5-p-methoxybenzoyl-1,2-dihydro-3H-pyrrolo[1,2-a]pyrrole-1-nitrile,
5-o-chlorobenzoyl-1,2-dihydro-3H-pyrrolo[1,2-a]pyrrole-1-nitrile,
5-m-chlorobenzoyl-1,2-dihydro-3H-pyrrolo[1,2-a]pyrrole-1-nitrile,
5-p-chlorobenzoyl-1,2-dihydro-3H-pyrrolo[1,2-a]pyrrole-1-nitrile,
5-o-fluorobenzoyl-1,2-dihydro-3H-pyrrolo[1,2-a]pyrrole-1-nitrile,
5-m-fluorobenzoyl-1,2-dihydro-3H-pyrrolo[1,2-a]pyrrole-1-nitrile,
5-p-fluorobenzoyl-1,2-dihydro-3H-pyrrolo[1,2-a]pyrrole-1-nitrile,
5-(3-chloro-2-thenoyl)-1,2-dihydro-3H-pyrrolo[1,2-a]pyrrole-1-nitrile,
5-(4-chloro-2-thenoyl)-1,2-dihydro-3H-pyrrolo[1,2-a]pyrrole-1-nitrile,
5-(5-chloro-2-thenoyl)-1,2-dihydro-3H-pyrrolo[1,2-a]pyrrole-1-nitrile,
5-(3-bromo-2-thenoyl)-1,2-dihydro-3H-pyrrolo[1,2-a]pyrrole-1-nitrile,
5-(4-bromo-2-thenoyl)-1,2-dihydro-3H-pyrrolo[1,2-a]pyrrole-1-nitrile,
5-(5-bromo-2-thenoyl)-1,2-dihydro-3H-pyrrolo[1,2-a]pyrrole-1-nitrile,
5-(3-methyl-2-thenoyl)-1,2-dihydro-3H-pyrrolo[1,2-a]pyrrole-1-nitrile,
5-(4-methyl-2-thenoyl)-1,2-dihydro-3H-pyrrolo[1,2-a]pyrrole-1-nitrile,
5-(5-methyl-2-thenoyl)-1,2-dihydro-3H-pyrrolo[1,2-a]pyrrole-1-nitrile,
5-(2-pyrroyl)-1,2-dihydro-3H-pyrrolo[1,2-a]pyrrolo-1-nitrile,
5-(N-methyl-2-pyrroyl)-1,2-dihydro-3H-pyrrolo[1,2-a]pyrrole-1-nitrile, and
5-(N-n-butyl-2-pyrroyl)-1,2-dihydro-3H-pyrrolo[1,2-a]pyrrole-1-nitrile, respectively.

EXAMPLE 1

To 3.5 g of concentrated hydrochloric acid (37% aqueous) there is added, at room temperature, 0.3 g of 5-(2-thenoyl)-1,2-dihydro-3H-pyrrolo[1,2-a]pyrrole-1-nitrile. The reaction mixture is purged with nitrogen and warmed to 100° C. The reaction mixture is agitated for seven minutes, while maintaining it under a nitrogen atmosphere, cooled to room temperature, and 10 ml of cold water (at 4° C.) is added thereto. The reaction mixture is then extracted with two 5 ml portions of ethyl acetate. The ethyl acetate extracts are combined, dried over anhydrous sodium sulfate, followed by complete evaporation of the solvent to yield 0.32 g (102%) of a crude product (93% pure as measured by high pressure liquid chromatography) containing 5-(2-thenoyl)-1,2-dihydro-3H-pyrrolo[1,2-a]pyrrole-1-carboxylic.

0.3 G. of the thus-obtained crude product is dissolved in 3 ml of hot ethyl acetate, cooled to 0° C. and collected by filtration to yield 0.2 g. (66.6%) of 5-(2-thenoyl)-1,2-dihydro-3H-pyrrolo[1,2-a]pyrrole-1-carboxylic acid having a melting point of 154°–155° C. Additional quantities of the product can be obtained for the mother liquor.

The 0.2 g of 5-(2-thenoyl)-1,2-dihydro-3H-pyrrolo[1,2-a]pyrrole-1-carboxylic acid obtained above is taken up in 3 ml of ethyl acetate and 1 ml of methanol and 0.2 g of decolorizing charcoal is added. The mixture is warmed to 50° C., followed by removal of the decolorizing charcoal by filtration and the methanol by distillation. The volume of the remaining solution is adjusted to about 2 ml by the addition of ethyl acetate, followed by cooling to 0° C., and collection by filtration to yield 0.17 g (85%) of 95% pure (by high pressure liquid chromatography) 5-(2-thenoyl)-1,2-dihydro-3H-pyrrolo[1,2-a]pyrrole-1-carboxylic acid having a melting point of 154°–155° C. Additional quantities of the product can be obtained from the mother liquors by standard crystallization work-up procedures.

Similarly, the replacement of the concentrated hydrochloric acid (37% aqueous) by a stoichiometric equivalent amount of sulfuric acid (40% aqueous) is productive of 5-(2-thenoyl)-1,2-dihydro-3H-pyrrolo[1,2-a]pyrrole-1-carboxylic acid.

EXAMPLE 2

To 3.5 g of 60% aqueous sulfuric acid there is added 0.5 g of 5-(2-thenoyl)-1,2-dihydro-3H-pyrrolo[1,2-a]pyrrole-1-nitrile. The reaction mixture is purged with nitrogen and warmed to 100° C. The reaction mixture is agitated for twelve minutes, whilst maintaining it under a nitrogen atmosphere, and 10 ml of cold water (at 4° C.) is added thereto. The reaction mixture is then extracted with two 5 ml portions of ethyl acetate. The ethyl acetate extracts are combined, dried over anhydrous sodium sulfate and concentrated to dryness to yield 0.5 g (92.7%) of a crude product (56% pure as measured by high pressure liquid chromatography) containing 5-(2-thenoyl)-1,2-dihydro-3H-pyrrolo[1,2-a]pyrrole-1-carboxylic acid.

0.4 G of the thus-obtained crude product is dissolved in 4 ml of methanol and 4 ml of water is added thereto. The mixture is agitated, followed by filtration. The solid material thus-obtained is taken up in 5 ml of ethyl acetate and 1 ml of methanol and 0.5 g of decolorizing charcoal is added thereto. The mixture is warmed to 50° C., the decolorizing charcoal is filtered off and the methanol is removed. The volume is then adjusted to about 2 ml by the addition of ethyl acetate, followed by cooling to 0° C., and filtration to yield 0.2 g (50%) 5-(2-thenoyl)-1,2-dihydro-3H-pyrrolo[1,2-a]pyrrole-1-carboxylic acid having a melting point of 147°–148° C. The melting point remained the same following a second crystallization from ethyl acetate and high pressure liquid chromatography indicated a purity of 79.8%.

EXAMPLE 3

To a mixture of 8 ml of glacial acetic acid and 8 ml of 85% phosphoric acid there is added 1.6 g of 5-(2-thenoyl)-1,2-dihydro-3H-pyrrolo[1,2-a]pyrrole-1-nitrile. The reaction mixture is purged with nitrogen and maintained, under a nitrogen atmosphere, at 110°–115° C. for two hours and twenty minutes. The reaction mixture is cooled and added to 50 ml of a mixture of 70% aqueous saturated sodium chloride solution-30% water. The material which precipitates is extracted with 10 ml of ethyl acetate and the extract is dried over anhydrous sodium sulfate and concentrated to remove nearly all the solvent, followed by the addition of 20 ml of hexane, filtration and vacuum drying at 45° C. to yield 1.66 g (96.3%) of a crude product (79% pure as measured by high pressure liquid chromatography) containing 5-(2-thenoyl)-1,2-dihydro-3H-pyrrolo[1,2-a]pyrrole-1-carboxylic acid.

1.4 G of the thus-obtained crude product is taken up in 15 ml of methanol and 0.5 g of decolorizing charcoal is added thereto, followed by agitation of the mixture for 15 minutes, filtration to remove the charcoal, and concentration to a volume of 5 ml., to which 5 ml of water is added. The aqueous mixture is agitated for ten minutes, followed by filtration to yield 1.1 g (78.6%) of product containing 5-(2-thenoyl)-1,2-dihydro-3H-pyrrolo[1,2-a]pyrrole-1-carboxylic acid.

1.0 G of the product, obtained immediately above, is taken up in 6 ml of hot ethyl acetate and the mixture is cooled to 0° C., agitated for 15 minutes, followed by filtration and washing with 2 ml of cold (0° C.) ethyl acetate to yield 0.6 g (60%) of 5-(2-thenoyl)-1,2-dihydro-3H-pyrrolo[1,2-a]pyrrole-1-carboxylic acid having a melting point of 158°–159° C. Additional quantities of product can be obtained from the ethyl acetate mother liquors by standard crystallization work-up procedures.

EXAMPLE 4

To 7.8 ml of 2-methoxyethanol there is added 0.8 g of 5-(2-thenoyl)-1,2-dihydro-3H-pyrrolo[1,2-a]pyrrole-1-nitrile. Following purgation with nitrogen, 1.6 ml of 20% aqueous potassium hydroxide solution is added and the reaction mixture, under a nitrogen atmosphere, is refluxed for a period of 48 minutes. The reaction solution is cooled to 20° C., 10 ml of water is added thereto, followed by washing with 20 ml of methylene chloride. To the aqueous portion, following extraction, there is added concentrated hydrochloric to attain a pH of about 3, and the material which precipitates is extracted with 20 ml of ethyl acetate, dried over anhydrous sodium sulfate and concentrated to dryness to yield 0.776 g (90%) of crude product containing 5-(2-thenoyl)-1,2-dihydro-3H-pyrrolo[1,2-a]pyrrole-1-carboxylic acid.

0.45 G of the crude product is taken up in 5 ml of hot ethyl acetate, cooled to 0° C. agitated for five minutes, and following filtration, washing with 2 ml of a 2:1 ethyl acetate-hexane mixture and vacuum drying at 45° C. there is obtained 0.32 g (71% w/w) of 5-(2-thenoyl)-1,2-dihydro-3H-pyrrolo[1,2-a]pyrrole-1-carboxylic acid having a melting point of 157°–159° C. Additional quantities of the product can be obtained by standard crystallization work-up procedures.

Similarly replacement of the potassium hydroxide by a stoichiometric equivalent amount of sodium hydroxide, or lithium hydroxide, is productive of 5-(2-thenoyl)-1,2-dihydro-3H-pyrrolo[1,2-a]pyrrole-1-carboxylic acid.

EXAMPLE 5

Following the procedures set forth in Examples 1, 2, 3, and 4 and substituting a stoichiometric equivalent amount of 5-benzoyl-1,2-dihydro-3H-pyrrolo[1,2-a]pyrrole-1-nitrile,
5-o-toluoyl-1,2-dihydro-3H-pyrrolo[1,2-a]pyrrole-1-nitrile,
5-m-toluoyl-1,2-dihydro-3H-pyrrolo[1,2-a]pyrrole-1-nitrile,
5-p-toluoyl-1,2-dihydro-3H-pyrrolo[1,2-a]pyrrole-1-nitrile,
5-p-methoxybenzoyl-1,2-dihydro-3H-pyrrolo[1,2-a]pyrrole-1-nitrile,
5-o-chlorobenzoyl-1,2-dihydro-3H-pyrrolo[1,2-a]pyrrole-1-nitrile,
5-m-chlorobenzoyl-1,2-dihydro-3H-pyrrolo[1,2-a]pyrrole-1-nitrile,
5-p-chlorobenzoyl-1,2-dihydro-3H-pyrrolo[1,2-a]pyrrole-1-nitrile,
5-o-fluorobenzoyl-1,2-dihydro-3H-pyrrolo[1,2-a]pyrrole-1-nitrile,
5-m-fluorobenzoyl-1,2-dihydro-3H-pyrrolo[1,2-a]pyrrole-1-nitrile,
5-p-fluorobenzoyl-1,2-dihydro-3H-pyrrolo[1,2-a]pyrrole-1-nitrile,
5-(3-chloro-2-thenoyl)-1,2-dihydro-3H-pyrrolo[1,2-a]pyrrole-1-nitrile,
5-(4-chloro-2-thenoyl)-1,2-dihydro-3H-pyrrolo[1,2-a]pyrrole-1-nitrile,
5-(5-chloro-2-thenoyl)-1,2-dihydro-3H-pyrrolo[1,2-a]pyrrole-1-nitrile,
5-(3-bromo-2-thenoyl)-1,2-dihydro-3H-pyrrolo[1,2-a]pyrrole-1-nitrile,
5-(4-bromo-2-thenoyl)-1,2-dihydro-3H-pyrrolo[1,2-a]pyrrole-1-nitrile,
5-(5-bromo-2-thenoyl)-1,2-dihydro-3H-pyrrolo[1,2-a]pyrrole-1-nitrile,
5-(3-methyl-2-thenoyl)-1,2-dihydro-3H-pyrrolo[1,2-a]pyrrole-1-nitrile,
5-(4-methyl-2-thenoyl)-1,2-dihydro-3H-pyrrolo[1,2-a]pyrrole-1-nitrile,
5-(5-methyl-2-thenoyl)-1,2-dihydro-3H-pyrrolo[1,2-a]pyrrole-1-nitrile,
5-(2-pyrroyl)-1,2-dihydro-3H-pyrrolo[1,2-a]pyrrole-1-nitrile,
5-(N-methyl-2-pyrroyl)-1,2-dihydro-3H-pyrrolo[1,2-a]pyrrole-1-nitrile,
5-(N-n-butyl-2-pyrroyl)-1,2-dihydro-3H-pyrrolo[1,2-a]pyrrole-1-nitrile, for
5-(2-thenoyl)-1,2-dihydro-3H-pyrrolo[1,2-a]pyrrole-1-nitrile, there are obtained
5-benzoyl-1,2-dihydro-3H-pyrrolo[1,2-a]pyrrole-1-carboxylic acid,
5-o-toluoyl-1,2-dihydro-3H-pyrrolo[1,2-a]pyrrole-1-carboxylic acid,
5-m-toluoyl-1,2-dihydro-3H-pyrrolo[1,2-a]pyrrole-1-carboxylic acid,
5-p-toluoyl-1,2-dihydro-3H-pyrrolo[1,2-a]pyrrole-1-carboxylic acid,
5-p-methoxybenzoyl-1,2-dihydro-3H-pyrrolo[1,2-a]pyrrole-1-carboxylic acid,
5-o-chlorobenzoyl-1,2-dihydro-3H-pyrrolo[1,2-a]pyrrole-1-carboxylic acid,
5-m-chlorobenzoyl-1,2-dihydro-3H-pyrrolo[1,2-a]pyrrole-1-carboxylic acid,
5-p-chlorobenzoyl-1,2-dihydro-3H-pyrrolo[1,2-a]pyrrole-1-carboxylic acid,
5-o-fluorobenzoyl-1,2-dihydro-3H-pyrrolo[1,2-a]pyrrole-1-carboxylic acid,
5-m-fluorobenzoyl-1,2-dihydro-3H-pyrrolo[1,2-a]pyrrole-1-carboxylic acid,
5-p-fluorobenzoyl-1,2-dihydro-3H-pyrrolo[1,2-a]pyrrole-1-carboxylic acid,
5-(3-chloro-2-thenoyl)-1,2-dihydro-3H-pyrrolo[1,2-a]pyrrole-1-carboxylic acid,
5-(4-chloro-2-thenoyl)-1,2-dihydro-3H-pyrrolo[1,2-a]pyrrole-1-carboxylic acid, 5-(5-chloro-2-thenoyl)-1,2-dihydro-3H-pyrrolo[1,2-a]pyrrole-1-carboxylic acid, 5-(3-bromo-2-thenoyl)-1,2-dihydro-3H-pyrrolo[1,2-a]pyrrole-1-carboxylic acid, 5-(4-bromo-2-thenoyl)-1,2-dihydro-3H-pyrrolo[1,2-a]pyrrole-1-carboxylic acid, 5-(5-bromo-2-thenoyl)-1,2-dihydro-3H-pyrrolo[1,2-a]pyrrole-1-carboxylic acid, 5-(3-methyl-2-thenoyl)-1,2-dihydro-3H-pyrrolo[1,2-a]pyrrole-1-carboxylic acid, 5-(4-methyl-2-thenoyl)-1,2-dihydro-3H-pyrrolo[1,2-a]pyrrole-1-carboxylic acid, 5-(5-methyl-2-thenoyl)-1,2-dihydro-3H-pyrrolo[1,2-a]pyrrole-1-carboxylic acid, 5-(2-pyrroyl)-1,2-dihydro-3H-pyrrolo[1,2-a]pyrrole-1-carboxylic acid, 5-(N-methyl-2-pyrroyl)-1,2-dihydro-3H-pyrrolo[1,2-a]pyrrole-1-carboxylic acid, and 5-(N-n-butyl-2-pyrroyl)-1,2-dihydro-3H-pyrrolo[1,2-a]pyrrole-1-carboxylic acid, respectively.

What is claimed is:

1. A compound of the formula:

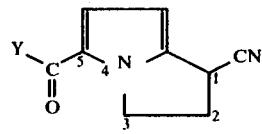

wherein Y is a moiety selected from the group consisting of

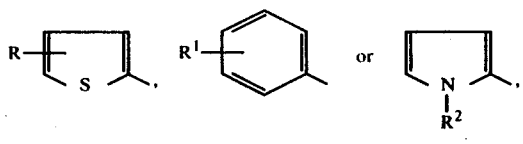

in which
R is hydrogen, methyl, chloro or bromo, the R substitution being at the 3, 4 or 5 positions of the thiophene ring,
$R^1$ is hydrogen, a lower alkyl group having 1 to 4 carbon atoms, a lower alkoxy group having from 1 to 4 carbon atoms, chloro, fluoro or bromo, the $R^1$ substitution being at the ortho, meta or para positions of the aroyl group, and $R^2$ is hydrogen or a lower alkyl group having from 1 to 4 carbon atoms.

2. According to claim 1, the compound 5-(2-thenoyl)-1,2-dihydro-3H-pyrrolo[1,2-a]pyrrole-1-nitrile.

3. According to claim 1, the compound 5-benzoyl-1,2-dihydro-3H-pyrrolo[1,2-a]pyrrole-1-nitrile.

4. According to claim 1, the compound 5-m-chlorobenzoyl-1,2-dihydro-3H-pyrrolo[1,2-a]pyrrole-1-nitrile.

* * * * *